US00PP12086P2

(12) United States Plant Patent
Bessho et al.

(10) Patent No.: US PP12,086 P2
(45) Date of Patent: Sep. 11, 2001

(54) CALIBRACHOA PLANT NAMED 'COLORBURST VIOLET'

(75) Inventors: Masao Bessho; Seiji Nakamura, both of Wade; Hitoshi Kojima, Osaga-gun, all of (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/310,195

(22) Filed: May 12, 1999

(51) Int. Cl.[7] ..... A01H 5/00
(52) U.S. Cl. ..... Plt./263
(58) Field of Search ..... Plt./356, 263

(56) References Cited

PUBLICATIONS

Fehr, Walter R. Pinciples of Cultivar Development pp. 28–33, 86–87, 361–366.*

* cited by examiner

*Primary Examiner*—Bruce R. Campell
*Assistant Examiner*—A Para
(74) *Attorney, Agent, or Firm*—Rothwell, Figg, Ernst & Manbeck

(57) ABSTRACT

Disclosed herein is a new and distinct Calibrachoa plant, and its parts, named 'Colorburst Violet' having a decumbent and compact habit. This plant grows vigorously with single flowers which have purple violet petals and a light yellow corolla throat. The plant is very resistant to rain, heat and drought conditions.

1 Drawing Sheet

BACKGROUND OF THE NEW PLANT

This invention relates to a new and distinct cultivar of Calibrachoa plant, hereinafter referred to by the name 'Colorburst Violet'. 'Colorburst Violet' is a new variety of Calibrachoa plant having a decumbent and compact habit. The plant grows vigorously and makes an excellent hanging basket. The invention's flowers are funnel shaped with five-fissured limbs, and a slight indent on each petal. The flowers are single with a diameter of 3.2–3.7 cm when fully open. The petals are purple violet (RHS 81A) with a light yellow corolla throat (RHS 6A). The plant is very resistant to rain, heat and drought. The plant grows and flowers best under low soil pH conditions (pH 5–6). Typically, flowers will stay open all day and night.

Classification of the current Petunia and Calibrachoa species is still in progress. The genus Petunia was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for Petunia in 1913. During the 1980's and 1990, H. J. Wijsman published a series of articles regarding the ancestry of *P. hybrida*, the Garden Petunia, and the inter-relationship of several species classified as Petunia. These studies revealed that *P. hybrida* and its ancestrial species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the Petunia genus, Wijsman and J. H. deJong proposed transferring the 14 chromosome species to the genus Stimoryne. Horticulturists opposed reclassifying the Garden Petunia and in 1986, Wijsman proposed the alternative of making *P. nyctaginiflora* the lectotype species for Petunia and transferring the 18 chromosome species to another genus. The I.N.G. Committee adopted this proposal. By 1990 Wijsman had transferred several species, including *P. parviflora* (=*C. parviflora*) to Calibrachoa, originally established by Llave and Lexarza in 1825. *Calibrachoa parviflora* (=*C. mexicana* la Lave & Lexarza ) is now the type species for the genus Calibrachoa.

As mentioned above, the classifcation of the current Petunia and Calibrachoa species is still in progress. New species are also being identified. Consequently a proper description has not been written for the Calibrachoa genus. Calibrachoa can, however, be distinguished from Petunia based on the higher chromosome number, chromosome morphology, plant branching habit and type of flower bud estivation. Whereas Petunia species bear a flower peduncle and one new stem from a node, Calibrachoa bear a flower peduncle and three stems. Petunia species have a cochlear corolla bud, a single outermost petal covers the other four, radially folded and terminally contorted petals. Calibrachoa flower buds are flat with all five petals linearly folded and the two lower petals forming a cover around the three other petals and fused together.

Asexual reproduction of 'Colorburst Violet' Calibrachoa originated from a hybridization made in 1996 in Kakegawa, Japan. The female parent was a cross between a bright purple-rose flowered, decumbent habit commercial variety named 'Liricashower Rose' (U.S. Plant Pat. No. 9,884) and breeder code C-13. Variety C-13 originated from a commercial market in South America. A single plant from this cross was then backcrossed to 'Liricashower Rose'. The initial cross-pollination was made in June, 1995. This $F_1$ seed was sown in February, 1996 and yielded 20 plants. From these 20 plants, one plant was selected and, during the summer of 1996, 'Liricashower Rose' was crossed to it to produce $BC_1$ seed. In August, 1996 the $BC_1$ seed was sown and yielded 50 plants. In December, 1996 five plants from these 50 plants were selected and intercrossed in a diallele pattern to produce a diallele derived BC2 population. In February, 1997 plants from the diallele derived BC2 population were selfed and the selfed seed produced from these plants was sown and yielded 50 plants. From these 50 plants, five plant lines were selected. In August, 1997 the five selected plant lines were vegetatively propagated and tested for easy reproducibility and stability of traits. One of these five plant lines was hence selected for vigorous growth, decumbent habit and purple violet flower color. In December, 1997, cuttings of this plant line were sent to California. During the spring and summer of 1998, plants were grown under the direction and supervision of the inventors for evaluation of stability of the line's desired traits. Plants were evaluated in hanging pots at Salinas, Calif., and in the field in Kakegawa, Japan.

The invention, 'Colorburst Violet' Calibrachoa, was determined by the inventors to have the characteristics, as herein described, firmly fixed. Plants were grown in plastic pots containing a peat moss-based media. The media pH was maintained between 5.0 and 6.0. Plants were grown under full sunlight in a greenhouse. The media was kept moist by overhead irrigation. A balanced fertilizer containing 20% nitrogen, 20% phosphorous and 20% potassium was applied three times per week through irrigation. The air temperatures ranged from 16° C. to 27° C. during the day and 13° C. to 18° C. at night.

Plants can be finished to full bloom in a variety of containers, including 10, 15, 20 and 41 cm diameter pots. The traits were taken from plants grown in a 41 cm diameter hanging basket with a maturity of 5 months. Two generations of successive propagation were performed between the final selection and collection of traits listed herein.

The new variety is distinguished from other Calibrachoa plants by its flower color, limited branching, decumbent habit and vigorous growth.

The closest commercial cultivar to this new variety that we are aware of is the petunia-like plant named 'Million Bells Trailing Blue'. The distinguishing characteristics which differentiate 'Colorburst Violet' from 'Million Bells Trailing Blue' are:

| | 'Colorburst Violet' | 'Million Bells Trailing Blue' |
|---|---|---|
| Flower Color: | Purple violet | Violet |
| Flower Size: | 3.2–3.7 cm | Smaller |
| Flower Throat Color: | Light yellow with purple veins | Light greenish yellow with violet veins |
| Growth Rate: | Very vigorous | Low vigor |

BRIEF DESCRIPTION OF THE DRAWINGS

The accompanying drawings serve by color photographic means to illustrate the new plant variety, 'Colorburst Violet'. The colors are represented as true as possible using conventional photographic procedures.

DETAILED DESCRIPTION OF THE NEW VARIETY

Figure 1:
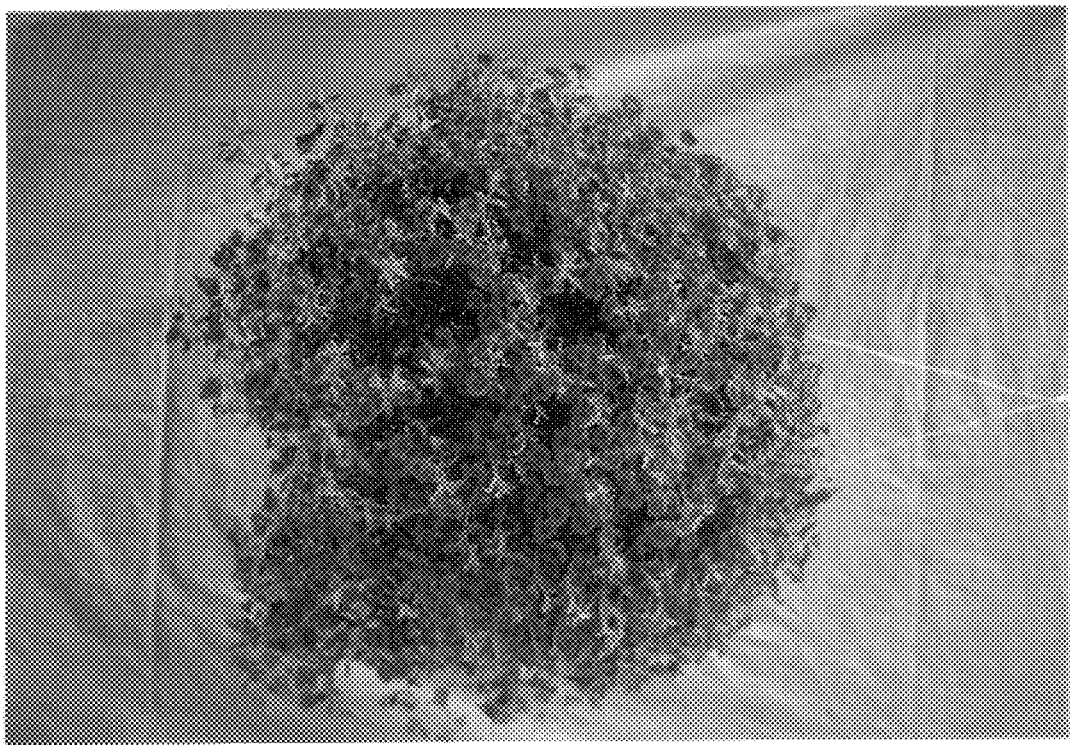
FIG. 1 is a close-up view of multiple blooms illustrating the decumbent, compact habit; abundant branching; and large profusion of blooms.
Figure 2:
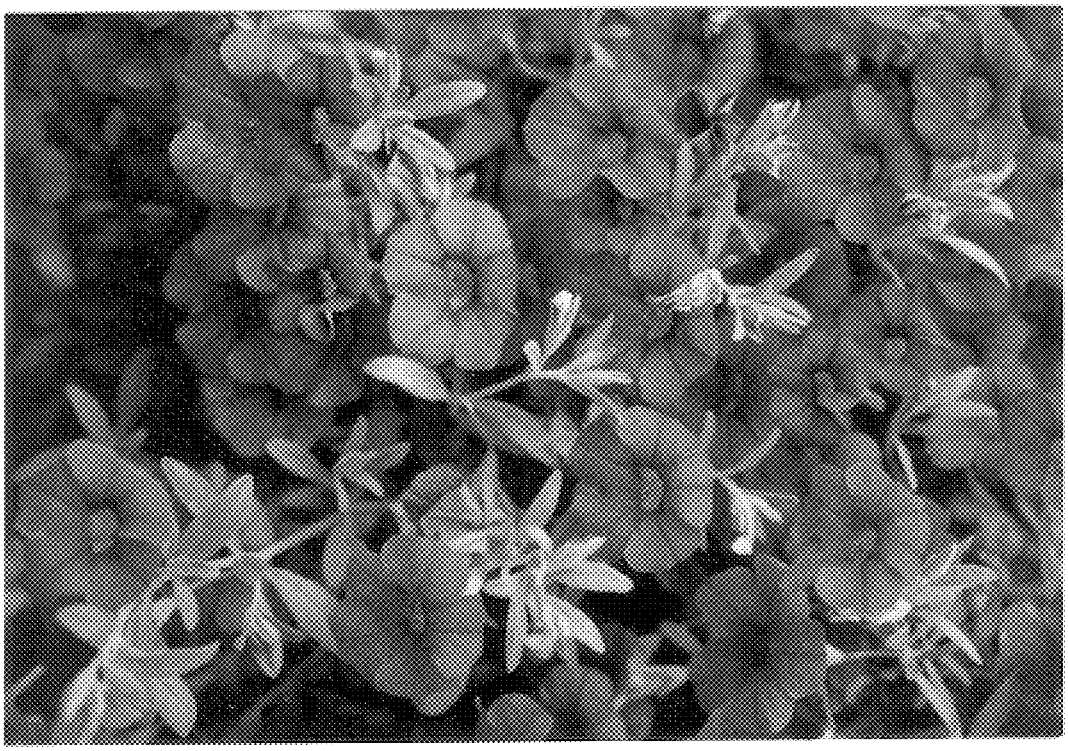
FIG. 2 is a view of the new cultivar after growing for several weeks in a hanging basket.

The following description is based on observations and measurements of pot grown plants in Salinas, Calif. Color designations were made according to The Royal Horticultural Society Colour Chart (R.H.S.) published by The Royal Horticultural Society of London, England.

Origin: Seedling.

Parentage:

*Female parent.*—(Liricashower Rose×C-13)× Liricashower Rose.

*Male parent.*—Liracashower Rose (U.S. Plant Pat. No. 9,884).

Classification:

*Family.*—Solanaceae.

*Genus.*—Calibrachoa.

*Botanical.*—Unknown; Calibrachoa species.

*Commercial.*—'Colorburst Violet'.

Plant:

*Growth habit.*—Decumbent.

*Plant height.*—14 cm.

*Plant spread.*—14 cm in all directions from the edge of the pot.

Stem:

*Thickness.*—2.0–3.0 mm.

*Color.*—Yellowish green (144C).

*Pubescence.*—Clear, soft, irregular in height and moderately dense.

*Branching.*—Limited.

*Internode length.*—1.5–2.0 cm.

Leaf:

*Shape.*—Lanceolate with acute tip; leaf margin is entire.

*Length* (*average*).—2.8 cm.

*Width* (*average*).—0.9 cm.

*Thickness.*—0.5–1.0 mm.

*Color.*—Upper leaf surface is green (137B) and lower leaf surface is green (138B).

*Pubescence.*—Present on both sides of the leaf surface; clear, soft, irregular in height and slightly dense.

Flower:

*Shape.*—Funnel shape, with five-fissured limb, slight indent on each petal; the corolla has radial symmetry with fused sepals and petals. There are 5 sepals measuring 1.4 cm×2.0 mm. The sepal shape is lanceolate with an acute tip; ovary is superior. Petals are fused at 5 mm from the tip of each petal.

*Lobation.*—None.

*Depth.*—2.7 cm.

*Diameter.*—3.2–3.7 cm when fully open.

*Color.*—Unopened stage: Light purple (77B); Mature upper petal is red-purple (81A); lower petal is red-purple (81B); main vein petal color is black (202A) with purple tinge; secondary vein petal color is red-purple (81A).

*Reproductive organs.*—One green yellow (154C) pistil, five green yellow (154C) stamens, 2 with long filaments bending upward over the pistil and 3 short filaments, anther is yellow and filaments are white.

*Fragrance.*—None.

*Fruit/seed.*—Not produced.

*Type.*—Perennial.

*Time for rooted cuttings.*—4 weeks.

*Disease, pest and cold tolerance.*—Plants are susceptible to Botrytis, powdery mildew, various stem and root rots and certain viruses such as Tobacco Mosaic Virus and Impatiens Necrotic Spotted Virus. Plants can be infected with aphids, leafminer, whitefly and various Lepidoptera. These plants are cold tolerant lasting through the winter under snow cover.

*Blooming habit.*—Plants begin to bloom with long days beginning in March and continuing through October. Each bloom lasts three days and stay open day and night. The blooms are fairly cold tolerant but will not withstand freezing temperatures.

*Bloom quantity.*—Mature plants grown in a 41 cm diameter hanging basket can have in excess of 700 open flowers at any given time and the inflorescence is solitary.

We claim:

1. A new and distinct cultivar of Calibrachoa plant named 'Colorburst Violet' as shown and described herein.

* * * * *